United States Patent [19]

Fettweis et al.

[11] Patent Number: 4,497,315

[45] Date of Patent: Feb. 5, 1985

[54] ORTHOPEDIC DEVICE FOR TREATING HIP DISPLEASURE AND HIP LUXATION

[75] Inventors: Ewald Fettweis, Aachen; Wolfgang Kindler, Cologne, both of Fed. Rep. of Germany

[73] Assignee: Otto Bock Orthopaedische Industrie KG, Duderstadt, Fed. Rep. of Germany

[21] Appl. No.: 364,661

[22] Filed: Apr. 2, 1982

[30] Foreign Application Priority Data

Apr. 7, 1981 [DE] Fed. Rep. of Germany ....... 3113981

[51] Int. Cl.³ .............................................. A61H 5/02
[52] U.S. Cl. .................................. 128/78; 128/80 A; 128/87 C
[58] Field of Search ............... 128/78, 80 R, 80 A, 128/80 F, 84 A, 87 C, 92 C; 3/2

[56] References Cited

U.S. PATENT DOCUMENTS

| 1,975,040 | 9/1934 | Groves ....................................... 3/2 |
| 3,260,259 | 7/1966 | Connelly ............................ 128/87 C |
| 3,274,997 | 9/1966 | Hewson, Jr. ........................ 128/87 C |
| 3,730,177 | 5/1973 | Thum ................................. 128/80 A |
| 4,108,168 | 8/1978 | Craig ................................. 128/80 A |

FOREIGN PATENT DOCUMENTS

| 2714272 | 6/1978 | Fed. Rep. of Germany ... 128/80 A |
| 665905 | 6/1979 | U.S.S.R. ........................... 128/80 A |

OTHER PUBLICATIONS

"The Management of Congenital Dislocation and Dysplasia of the Hip by Means of a Special Splint", *The Journal of Bone and Joint Surgery*, vol. 39A, No. 1, Jan. 1957, pp. 97-105.

*Primary Examiner*—Richard J. Apley
*Assistant Examiner*—David J. Brown
*Attorney, Agent, or Firm*—Michael J. Striker

[57] ABSTRACT

An orthopedic device for hip displeasure or hip luxation has a pelvic basket, two thigh holders, two thigh-guiding members connected with the thigh holders and the pelvic basket and a universal joint provided between the pelvic basket and the thigh-guiding members, located in the region of the natural hip joint, and having a moveable joint part arresting in each angular position.

13 Claims, 4 Drawing Figures

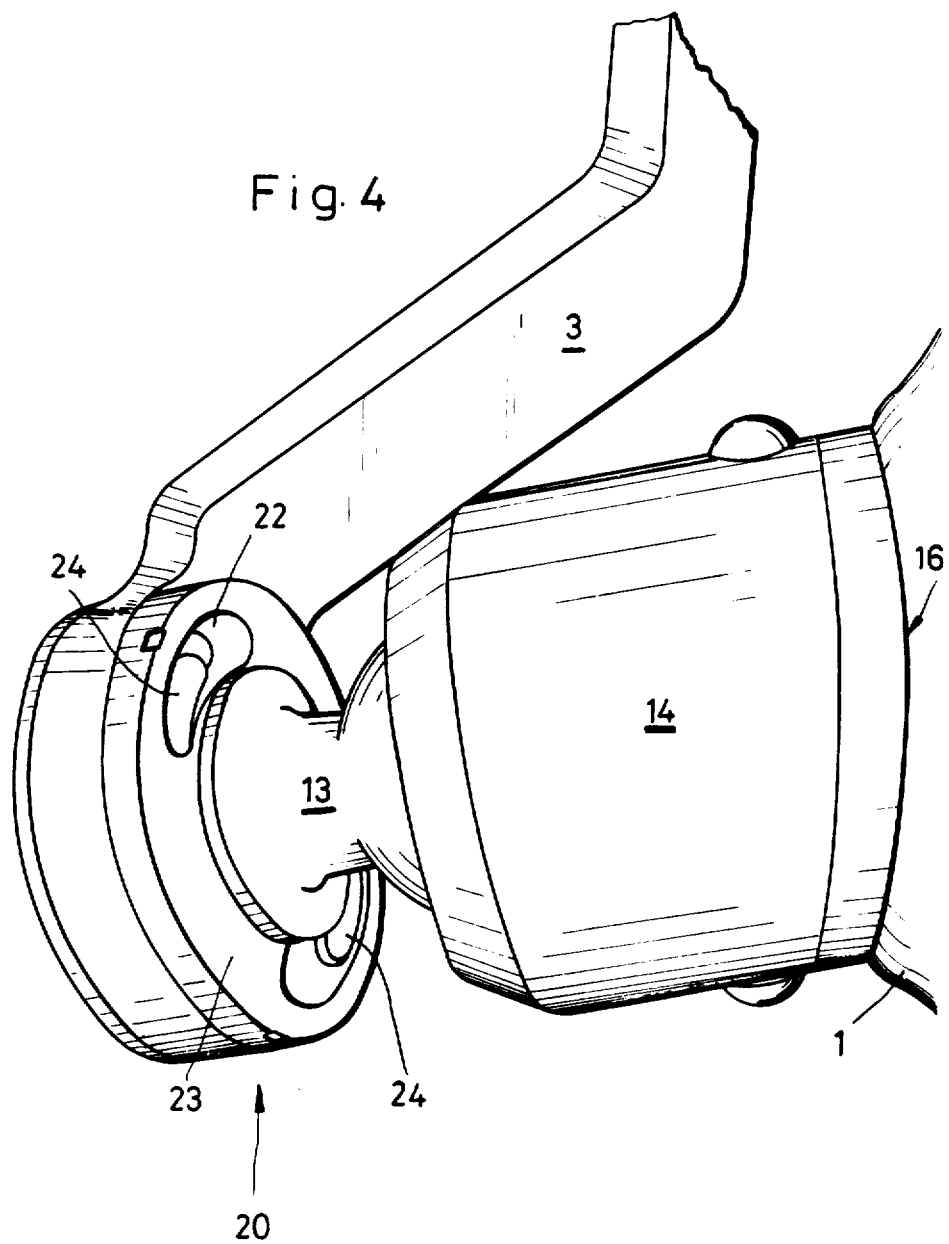

27# ORTHOPEDIC DEVICE FOR TREATING HIP DISPLEASURE AND HIP LUXATION

BACKGROUND OF THE INVENTION

The present invention relates to an orthopedic device for treating hip displeasure and hip luxation.

Devices of the above-mentioned general type are known in the art and known orthopedic device for treating hip displeasure or hip luxation has a pelvic basket and two thigh holders each mounted on one end of a thigh-guiding member whose other end is pivotally connected with the pelvic basket. Such a device is disclosed, for example, in the German Auslegeschrift No. 2,714,272. The pelvic basket in this device is considerably raised in its lateral regions and has at its lower end a spreading web with an upwardly expanding projection shaped as a bracket whereby a thigh opening is formed in the lower region of the pelvic basket. A belt with a burdock-type lock is connected with the pelvic basket at its upper end. Thigh-guiding members are pivotally mounted at the side of the pelvic basket with the aid of a screw which simultaneously forms the axis of rotation of the thigh-guiding member. Because of this pivotability, a child can bring the bone to a suitable position for walking, crawling and lying.

The thigh-guiding members are composed of two flat bars which are displaceable in longitudinal direction relative to one another and fixable in a stepless manner to one another. Thereby the guiding members are longitudinally adjustable in a stepless manner and can be adjusted in dependence upon the thigh length of the patient. Mounting means of the thigh-guiding members and therefore the axes of rotation of the latter are located above the so-called thigh openings, whereas both axes of rotation are approximately in alignment with one another. The thigh-guiding members are bent with an obtuse angle of approximately 180°, so that they intersect a straight line of the sagittal plane of the pelvic basket located in the longitudinal axis of the thigh-guiding members in immovable position, at an angle α of approximately 35°. The spreading angle holds the abduction of 35° during bending from zero to 90°.

Treatment of hip displeasure and hip luxation in newborns is performed in two phases. The first phase includes reposition of the hip joint head or the head core (in the originally formed joint head) into the seat. The second phase includes retention, i.e. fixing of the corrected joint head in position which is favorable for maturing of the joint. The retention is performed mainly by fixation of the bone with a gypsum bandage in a position prescribed by a physician. For a long time the experts were concerned with determination of an angular position which is optimal for curing of the hip joint. Despite extensive clinical and experimental research, they are still far from a uniform treatment technique. As before, the value of the angle selected for retention as well as the position of the bones are controversial. Research has shown that after long fixation of an extremity in the gypsum bandage, irreversible damage takes place not only on bones, but also in muscles, vains and ligaments. It has been recognized that these damages are seldom attributable to the gypsum bandage itself, but more often are attributed to the bone holders which receive the gypsum bandage, particularly because of the strong staying. There were also attempts during reposition and retension of the hip joints to reduce the duration in the gypsum bandage and to avoid the regidity of the fixation of the same. For this purpose, numerous casts and bandages were developed. Designers and physicians provide information about many achievements in this field. The only conclusion which can be drawn from this is that the correct bone position during the reposition as well as the retension is different from case to case, so that the treatment is performed not in a standard position but instead in an individually determined position of bones. In addition, all known casts and bandages allow more or less only a certain treatment position and thereby narrow the treatment posibilities of the physician in very disadvantageous manner for the patients.

U.S. Pat. No. 3,068,862 discloses a spreading device which makes possible only one independent from a physician and very strong spreading position of the child's bones. A comparable device is disclosed also in the German Auslegesschrift No. 1,263,219. A substantially flexible construction is described in the German Offenlegungsschrift No. 2,018,240. The starting point of the present invention is the above-mentioned German Auslegesschrift No. 2,714,272. In this reference the thigh-guiding members or casts are pivotably articulately connected on the pelvic basket. However, the pivoting is performed exclusively about fixed and aligned pivot axes, so that the above-mentioned abduction is always held with an angle of 35°. The treating physician has no possibility to change the spreading position during the treatment in a stepless manner. There is also the disadvantage that the thigh-guiding members are freely pivotable. Arresting and/or limiting of the pivotable movement within a predetermined angular region is not possible. Another disadvantage is the arrangement of both pivot axes so that they are not located in the region of the natural hip joint. The spreading device does not allow arrangement of the shank-guiding members with their respective shank holders. Because of the raised-up lateral regions of the pelvic basket, as well as the spreading web provided at its front side, lying of the child, particularly for changing diapers or clothes is very difficult. Because the spreading web is arranged on the front side of the pelvic basket, a certain spreading position of the bone of the patient is predetermined with this spreading device, so that in the sense of this basic disadvantage this device does not differ from the above-mentioned constructions. Comparative tests have shown that animals including babies, can be subdivided into two groups in dependence upon the birth conditions: those tending to remain in a nest and those tending to leave the nest. The first group is at a lower organization stage, whereas the second group belongs to a higher organization and the brain of the babies of the second group is completely developed. Because of its highly developed brain, the man must be qualified as belonging to the animals with a tendency to leave the nest. However, it is not the case. The reasons for this is that with its nine months he still has to be considered as prematurely born and first matures to be one having the tendency to leave the nest only after the following twelve months. After the birth, mother and child forms a similar biological unity as during the pregnency. As a result of this, the organs which have not matured in the mother's womb, for example the hip joint, must be retained in a position similar to the position of these organs in pre-birth conditions in order to complete the process of maturing without distortions. When this does not take place, outer mechanical influences on immature hip joints can dislocate them.

These views can also be proved by research in anthropology. During the tribal time of the human history, mothers carried their children on their bodies which is also known today in many nations. Hip luxation is extremely seldem there. Since in natural conditions of babies, the mother and not the baby has a channel forming the only surrounding of the child, a holding apparatus for bones must be adapted to life on the mother's body. This is defined by Doctor Fettweis as sit-squat position for treating the hip displeasure and hip luxation in connection with a gypsum bandage.

SUMMARY OF THE INVENTION

Accordingly, it is an object of the present invention to provide an orthopedic device which avoids the disadvantages of the prior art.

More particularly, it is an object of the present invention to provide an orthopedic device which is improved as compared with the known devices and allows considerably greater treatment field.

In keeping with these objects and with others which will become apparent hereinafter, one feature of the present invention resides, briefly stated, in an orthopedic device in which a joint formed as a universal joint is arranged in the region of the natural hip joint between a pelvis basket and thigh-guiding members, and a moveable joint part of this joint can be arrested in any angular position.

In accordance with another advantageous feature of the present invention, a further universal joint is provided between the moveable joint part of the first-mentioned universal joint and the thigh-guiding member, and the thigh-guiding member is pivotable about the axis of the further universal joint independently upon the position or arresting of the first-mentioned universal joint and can also be arrested in the desired pivotal position.

Contrary to the known orthopedic devices of this type, the artifical hip joint is arranged in the region of the natural hip joint and is also formed as a universal joint similar to the latter. The shape and arrangement of the artifical hip joint is designed so that each position required for treatment can be adjusted in a stepless manner. The physician is thereby not limited to a completely predetermined spreading position provided by this spreading device and unchangeable, for the bones of the patient. The additional universal joint which is combined with the first-mentioned joint makes possible to provide for freedom of movement in the hip joint in the angular position obtained by the first-mentioned universal joint.

In accordance with still another especially advantageous feature of the present invention, when the first-mentioned universal joint is arrested, the thigh-guiding members are freely rotatable about the axes of the first-mentioned universal joints only within a limited angular region. Thereby a stepped release of the movement of the hip joint is obtained.

In accordance with a further advantageous feature of the present invention, the value of the above-mentioned angular region is adjustable.

Still a further feature of the present invention which provides for a suitable construction, is that a joint housing which receives the moveable joint part of the first-mentioned universal joint is formed as a rotation symmetrical bush connected with an inclined bottom. The latter is mounted on the pelvic basket.

A next advantageous feature of the present invention provides for a possibility to change the angular arrangement of the first-mentioned universal joint and thereby also the further universal joint relative to the pelvic basket. In accordance with this feature the housing, relative to its bush axis, can be fixed in different pivotal positions on the pelvic basket.

In order to further adapt the movements during the utilization of the orthopedic device to the natural movements, it is advantageous when both housings of the first-mentioned universal joints are arranged at an angle of approximately 90°. The main purpose of this is to project the pivot point for the pivotal movement of the thigh-guiding members to the natural hip joint.

Thigh-guiding members with shank holders can be releasably articulately connected with the thigh-guiding members. The articulated connection is located at the height of the knee joint. During stretching of these shank-guiding members or holders, a pressure can be applied to the hip joint. For adaptation to the patient, it is advantageous when the thighholders and shank-holders are longitudinally moveably mounted on their guiding members.

For putting the child into the device, it is advantageous when the pelvis basket and thigh and shank holders are formed as half shells and the pelvic basket is closeable by an abdomenal plate articulately connected therewith. The abdomenal plate can be formed as a relatively flat half shell which allows easy change of a diaper. Thigh openings through which the bones of the child extend can be dispensed with in the inventive construction completely. The abdomenal plate which can be closed advantageously by a burdac-type lock and the like, can be formed sufficiently wide to guarantee a reliable and simple fixed position of the child in the device.

It is also advantageous when all structural elements are composed of materials which do not produce shadows on an X-ray picture, so that during the reposition optical sealed and picture forming element can be used, in contrast to the gypsum bandage, to use weak rays in the organically sensible region of the patient body.

The new orthopedic device is particularly suitable for treating hip displeasure in the position of the sit-squat in accordance with Doctor Fettweis. Further, this device is also suitable for performing other treatments. No treatment methods are limiting for this construction. The construction is designed so that the physician can perform application of the device without aid of a mechanic.

The pelvic basket as well as the thigh and shank holders are advantageously connected by screws with mechanical pivots or guiding members so that the above-mentioned half-shell parts can be easily exchanged and thereby easily adapted to respective patients.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIG. 4 is an enlarged view of a joint within a pelvic basket and a thigh-guiding member.

DESCRIPTION OF A PREFERRED EMBODIMENT

Figure 1:
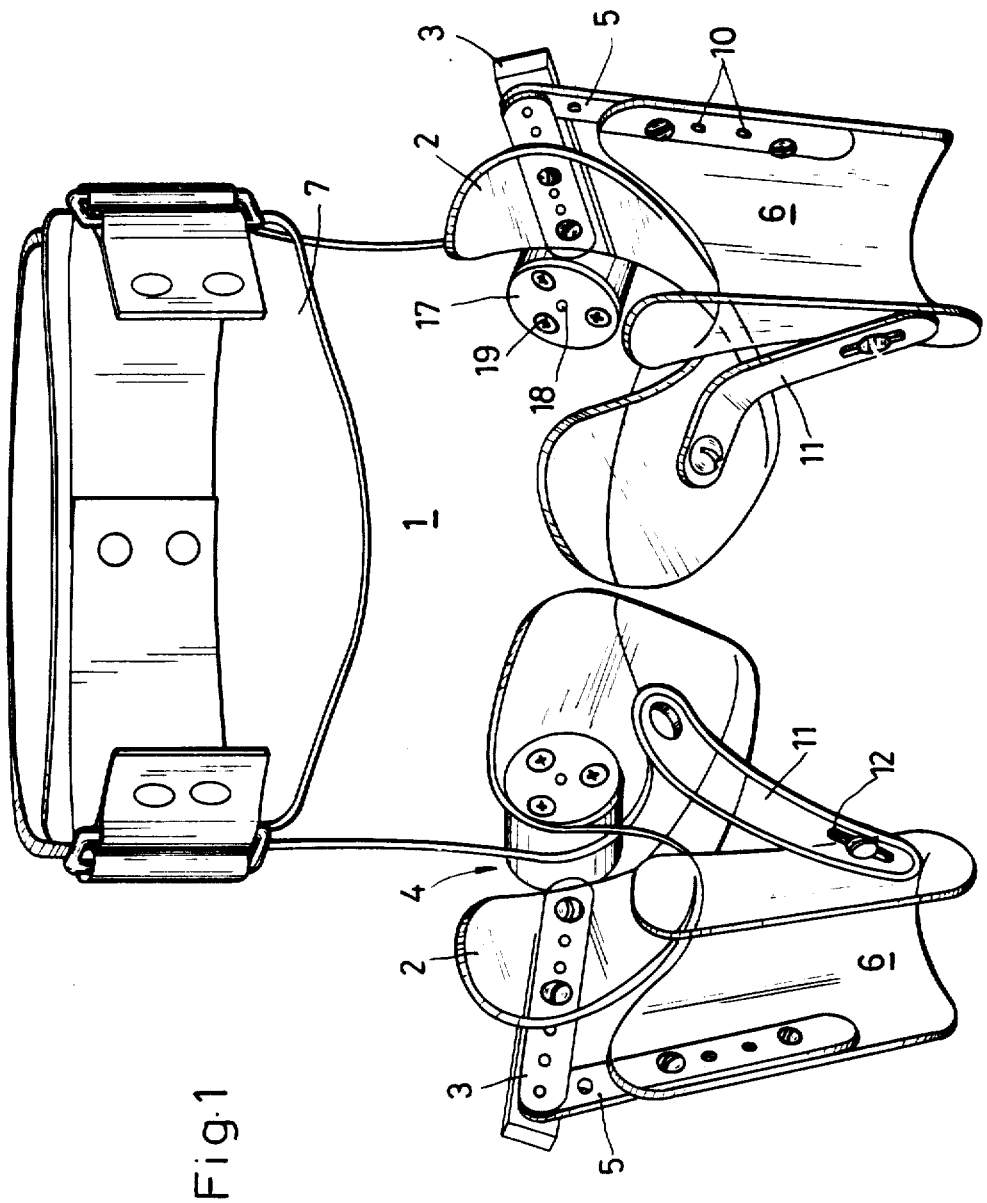
FIG. 1 is a front view of an orthopedic device in accordance with the present invention.

An orthopedic device for treating hip displeasure and hip luxation has a pelvic basket 1 and two thigh holders 2 each mounted on one end of a respective one of thigh-guiding members 3. The other end of the thigh-guiding member is pivotally connected with the pelvic basket 1 via a joint 4 which is arranged in the region of the natural hip joint and formed as a universal joint.

A shank-guiding member 5 with a shank holder 6 is articulately and releasably connected with the thigh-guiding member 3. The pelvic basket 1, as well as the thigh holders 2 and the shank holders 6 are formed approximately as half shells. The pelvic basket 1 is closeable by an abdomenal plate articulately connected therewith. Elongated slots 8 are provided in the thigh-guiding members 3. Screws 9 extend through the elongated slots 8, and thereby the thigh holders 2 are retained displaceable relative to the thigh-guiding members 3 and can be arrested in any desired position. Different openings 10 are provided in the shank-guiding members 5, and not-shown mounting means extend through the openings 10 to fix the shank holders 6. The openings 10 also make possible longitudinal displacement of the shank holders 6 relative to their guiding members 5. The shank holders 6 are additionally fixed by a shackle 11 to the associated thigh holder 2. A longitudinal slot 12 provided in the shackle 11 makes possible pivoting of the shank holders 6 relative to the thigh holders 2.

Figure 2:
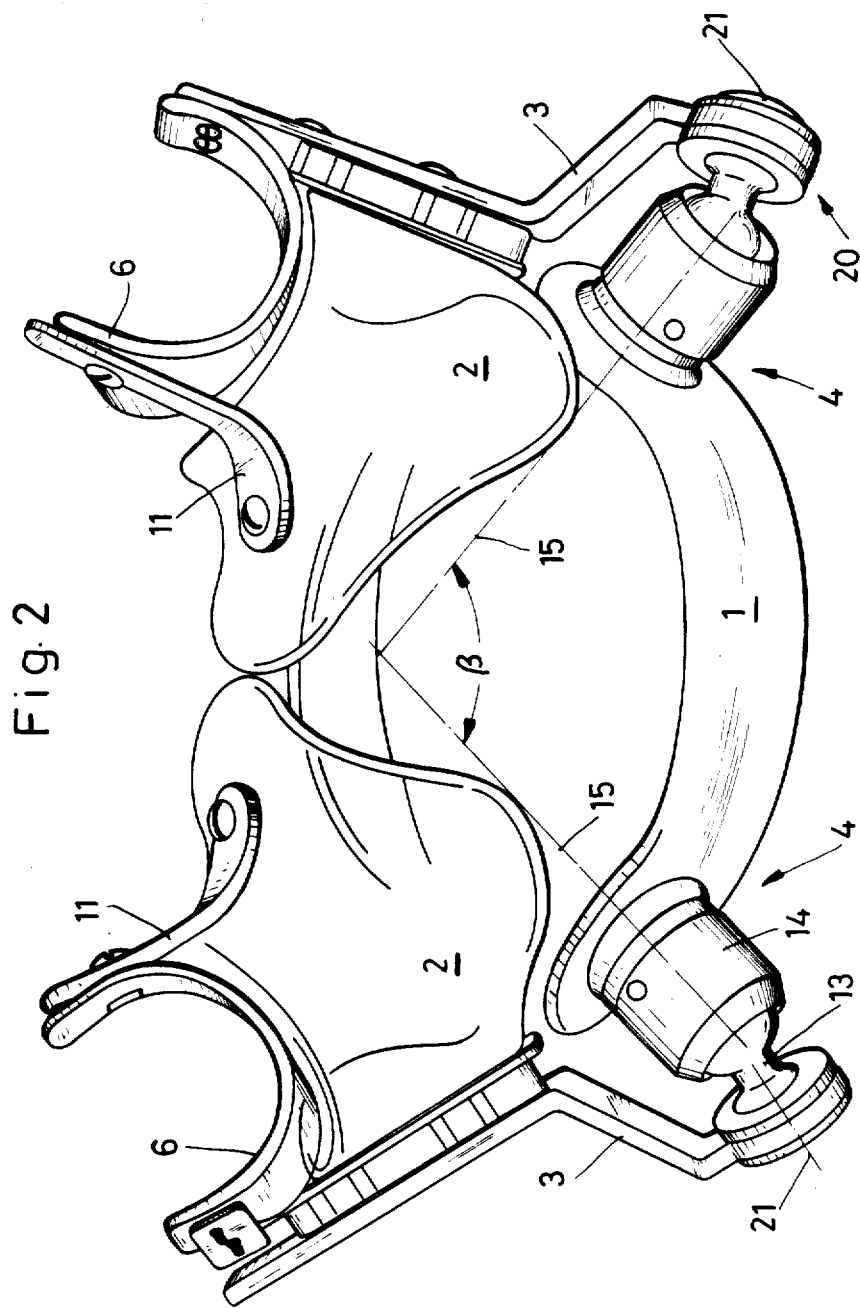
FIG. 2 is a view from below of the orthopedic device of FIG. 1.

The joint 4 includes a moveable joint part 13, a joint housing 14 receiving the joint part 13 and formed as a rotation-symmetrical bush, and a bottom 16 extending at an angle to an axis 15 of the bush and mounting the latter on the pelvic basket 1. As can be seen from FIG. 1, the mounting is performed via a tightening screw 17 arranged at the inner side of the pelvic basket 1, whereas the joint housing 14 pivotally engages in the tightening screw 17 by a centering pin 18 extending through the wall of the pelvic basket 1. Fixation is performed by three tightening screws 19. After releasing of the tightening screws 19, the joint housing 14 can be turned about its pin 18 by approximately 120° and fixed in the desired position by the tightening screws 19 on the pelvic basket 1. Thereby, the angular location of the joint relative to the pelvic basket is changed. As can be seen from FIG. 2, the bush axes 15 of both joint housing 14 are inclined relative to one another by an angle β of approximately 90°.

Figure 3:
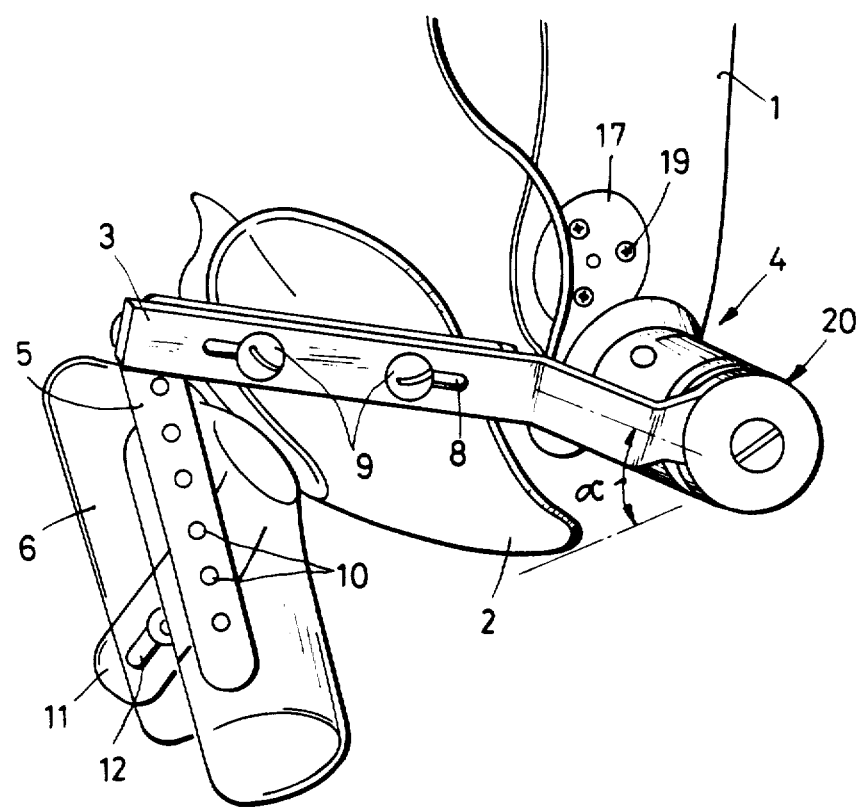
FIG. 3 is a sectioned lateral view of the orthopedic device of FIG. 1, in section.

A further hinge joint 20 is arranged between the moveable joint part 13 of the joint 4 and the thigh-guiding member 3. The thigh-guiding member is pivotable about an axis 21 of the joint 20 independently of the position or arresting of the universal joint 4, and is arrestable in the desired angular position. The axes 21 are formed by screws which extend in the moveable joint part 13 and act there on not-shown clamping means. By tightening of the screws forming the axes 21, arresting of the moveable joint parts 13 inside the joint housing 14 takes place in any desireable angular position. Independently of the arresting of the moveable joint part 13, the thigh-guiding member 3 can be pivoted about the axis 21 of the joint 20 and over a limited angular region α, as can be seen in FIG. 3. Limiting of the angular region α is performed by a slot 22 which has a shape of a circular arc, as shown in FIG. 4, and is provided in a disk 22 fixably connected with the moveable joint part 13. A guiding cam 24 engages in the slot 22 and is seated at the inner side of the thigh-guiding member 3. The disk 23 can be connected with the moveable joint part 13, for example by screws. By replacing of this disk with a disk having longer or shorter slots 22, the value of the above-mentioned angular region α can be adjusted.

It will be understood that each of the elements described above, or two or more together, may also find a useful application in other types of constructions differing from the types described above.

While the invention has been illustrated and described as embodied in an orthopedic device for treating hip displeasure and hip luxation, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. An orthopedic device for treating hip displeasure and hip luxation, comprising
   a pelvic basket;
   two thigh holders;
   two thigh-guiding members having two ends, one end of each of said thigh guiding members being pivotally connected with said pelvic basket, whereas the other end of the same is connected with a respective one of said thigh holders;
   two joints each provided in the region of a natural hip joint for providing said pivotal connection between said pelvic basket and a respective one of said thigh-guiding members and formed as a universal joint, each of said joints having a moveable joint part which can be arrested in any angular position; and
   a further universal joint provided between the moveable joint part of each of said first-mentioned universal joints and a respective one of said thigh-guiding members, and having an axis.

2. An orthopedic device as defined in claim 1, wherein each of said further universal joint has an axis and is arranged so that a respective one of said thigh guiding members can be pivoted about the axis of said further universal joint and arrested in a desired position independently of a position or arresting of a respective one of said first-mentioned universal joints.

3. An orthopedic device as defined in claim 2, wherein each of said thigh-guiding members is connected with a respective one of said further universal joints so that when each of said first-mentioned universal joints is arrested, a respective one of said thigh-guiding members is freely pivotable about the axis of a respective one of said further universal joints only within a limited angle.

4. An orthopedic device as defined in claim 3, wherein said angle of pivoting of said thigh-guiding members is adjustable.

5. An orthopedic device as defined in claim 1, wherein each of said universal joints includes a joint housing which receives said moveable joint member and is formed as a rotation-symmetrical bush having an axis, and a bottom extending at an angle to the axis of said bush.

6. An orthopedic device as defined in claim 5, wherein the bush of each of said universal joints is mounted on said pelvic basket via the bottom of the same universal joint.

7. An orthopedic device as defined in claim 6, wherein the joint housing of each of said universal joints is fixable in a plurality of pivotal positions relative to the axis of the bush, on said pelvic basket.

8. An orthopedic device as defined in claim 5, wherein the axis of the bushes of said universal joints are inclined to one another at an angle equal to substantially 90°.

9. An orthopedic device as defined in claim 1; and further comprising two shank-guiding members each having a shank holder and releasably articulately connected with a respective one of said thigh-guiding members.

10. An orthopedic device as as defined in claim 9, wherein said thigh holders and said shank holders are mounted on said thigh-guiding members and said shank-guiding members, respectively, displaceable in a direction of elongation of the latter.

11. An orthopedic device as defined in claim 9, wherein said pelvic basket, said thigh holders and said shank holders are formed as half shells.

12. An orthopedic device as defined in claim 1; and further comprising an abdominal plate articulately connected with said pelvic basket so that said pelvic basket is displaceable over said abdominal plate.

13. An orthopedic device as defined in claim 9, wherein said pelvic basket, said holders, said guiding members and said universal joints are composed of a material which does not produce shadows on an X-ray picture.

* * * * *